(12) United States Patent
Choi et al.

(10) Patent No.: US 10,758,546 B2
(45) Date of Patent: Sep. 1, 2020

(54) TRANSDERMAL DELIVERY SYSTEM CONTAINING GALANTAMINE OR SALTS THEREOF

(71) Applicants: Industry-Academic Cooperation Foundation, Chosun University, Gwangju (KR); TAHO Pharmaceuticals Ltd., Taipei (TW)

(72) Inventors: Hoo-kyun Choi, Gwangju (KR); Myung-kwan Chun, Seoul (KR)

(73) Assignees: Industry-Academic Cooperation Foundation, Gwangju (KR); TAHO Pharmaceuticals Ltd., Taipei (TW)

(*) Notice: Subject to any disclaimer, the term of this patent is extended or adjusted under 35 U.S.C. 154(b) by 0 days.

(21) Appl. No.: 15/215,302

(22) Filed: Jul. 20, 2016

(65) Prior Publication Data

US 2016/0339038 A1 Nov. 24, 2016

Related U.S. Application Data

(63) Continuation of application No. 13/985,994, filed as application No. PCT/KR2012/001186 on Feb. 17, 2012, now abandoned.

(30) Foreign Application Priority Data

Feb. 18, 2011 (KR) .................. 10-2011-0014530

(51) Int. Cl.
*A61K 31/55* (2006.01)
*A61K 9/70* (2006.01)
*A61K 47/32* (2006.01)
*A61K 47/14* (2017.01)

(52) U.S. Cl.
CPC ............... *A61K 31/55* (2013.01); *A61K 9/70* (2013.01); *A61K 9/7023* (2013.01); *A61K 9/7053* (2013.01); *A61K 47/14* (2013.01); *A61K 47/32* (2013.01)

(58) Field of Classification Search
None
See application file for complete search history.

(56) References Cited

U.S. PATENT DOCUMENTS

| | | | |
|---|---|---|---|
| 5,089,267 | A | 2/1992 | Hille et al. |
| 5,700,480 | A | 12/1997 | Hille et al. |
| 5,932,238 | A | 8/1999 | Opitz |
| 6,558,696 | B1 | 5/2003 | Hille et al. |
| 8,383,149 | B2 | 2/2013 | Audett et al. |
| 8,715,715 | B2 | 5/2014 | Ryoo et al. |
| 2006/0257461 | A1 | 11/2006 | Jansen et al. |
| 2007/0098771 | A1 | 5/2007 | Audett et al. |
| 2007/0104771 | A1 | 5/2007 | Audett et al. |
| 2007/0064407 | A1 | 6/2007 | Gargiulo et al. |
| 2007/0259028 | A1 | 11/2007 | Ito |
| 2009/0175929 | A1 | 7/2009 | Terahara et al. |
| 2015/0352058 | A1 | 12/2015 | Mo |

FOREIGN PATENT DOCUMENTS

| | | |
|---|---|---|
| EP | 2 676 663 A2 | 12/2013 |
| WO | WO-2007064407 | 6/2007 |

OTHER PUBLICATIONS

Md. Kamal Hossain, et al., Formulation and In vitro Evaluation of Transdermal Drug delivery System for Glantamine, Journal of Pharmaceutical Investigation, Feb. 18, 2011, vol. 41, No. 1, pp. 1-7.
Chun-Woong Park, et al. Investigationof formuatlion factors affecting in vitro and in vivo characteristics of a galantantamine transdermal system, International Journal of Pharmaceutics, Jul. 5, 2012, vol. 436, pp. 32-40.
Tzu-Yung Wu, et al., Development and Optimization of a One-Day Transdermal Galantamine Patch for the Treatment of Alzheimer's Disease, AAPS Poster No. T2271, Nov. 12, 2013.
Non Final Office Action in corresponding U.S. Appl. No. 13/985,994, dated Jun. 9, 2015.
Coyle, J., Kershaw, P., Galantamine, a cholinesterase inhibitor that allosterically modulates nicotinic receptors: effects on the course of Alzheimers disease. Biol. Psychiatry. (2001) 49, pp. 289-299.
Zarotsky, V., Sramek, J.J., Cutler, N.R., Galantamine hydrobromide: an agent for Alzheimer's disease. Am. J. Health-Syst. Pharm. (2001) 60, pp. 446-452.
Scott, L.J., Goa, K.L., Galantamine: a review of its use in Alzheimer's disease. Drugs. (2000) 60, pp. 1095-1122.
Thomas, B.J., Finnin, F.C., The transdermal revolution. Drug Discov. Today (2004) vol. 9, No. 16, pp. 697-703.
Walters, K.A., Walker, M., Olejnik, 0., Non-ionic surfactant effects on hairless mouse skin permeability characteristics. J. Pharm. Pharmacol. (1987) 40, pp. 525-529.
Williams, A.C., Barry, B.W., Pernetration enhancers. Adv. Drug Deliver. Rev. (2004) 56, pp. 603-618.
Ang, C., Fen, H.E., Sub, H.E., 2006. Pharmacokinetics of galantamine Hbr in plasma and brain of mice. Chin. J. Pharm. 37, 55-61.
Choi, H-K., Angello, J., The Mathematical analysis and optimization of a flow through diffusion cell system. Pharm. Res., (1994), 11, pp. 595-599.
Subedi, R.K., Jang, J.H., Kim, Jae-II, Park, Y.J., Choi, H.-K., Formulation and evaluation of transdermal patch containing sibutramine. J. Kor. Pharm. Sci., (2010), vol. 40, No. 1, pp. 33-38.
Kim, J.H., Cho Y.-J., Choi, H.-K., Effect of vehicles and pressure sensitive adhesives on the permeation of tacrine across hairless mouse skin. Int. J. Pharm. (2000), 196, pp. 105-113.
Morimoto, Y., Kokubo, T., Sugibayashi, K., Diffusion of drug in acrylic type pressure sensitive adhesive matrix. II. Influence 5 of interaction. J. Control. Release, (1991) 18, pp. 113-121.

(Continued)

*Primary Examiner* — David J Blanchard
*Assistant Examiner* — Daniel F. Coughlin
(74) *Attorney, Agent, or Firm* — Leason Ellis LLP

(57) ABSTRACT

The present invention provides a transdermal delivery system, which comprises a drug-containing matrix layer comprising: galantamine or its pharmaceutically acceptable salt as an active ingredient; and a styrene-butadiene-styrene copolymer or a styrene-isoprene-styrene copolymer as an adhesive.

7 Claims, 3 Drawing Sheets

(56) References Cited

OTHER PUBLICATIONS

Furuishi, T., lo, T., Fukami, T., Suzuki, T., Tomono, K., Formulation and in vitro evaluation of pentazocine transdermal delivery system. Biol. Pharm. Bull., (2008) 31(7), pp. 1439-1443.

Wokovich, AM., Prodduturi, S., Doub, W.H., Hussain, AS., Buhse, L.F ., Transdermal delivery system (TDDS) adhesion as a critical safety, efficacy and quality attribute. Eur. J. Pharm. Biopharm. (2006) 64, pp. 1-8.

Chun-Woong Park, et al, "Investigation of formulation factors affecting in vitro and in vivo characteristics of a galantamine transdermal system", International Journal of Pharmaceutics, 436 (2012), pp. 32-40.

Md. Kamal Hossain, et al., "Formulation and *In vitro* Evaluation of Transdermal Drug Delivery System for Galantamine", Journal of Pharmaeutical Investigation, (2011), vol. 41, No. 1, pp. 1-7.

G. S. J. Mannens, et al., "The Metabolism and Excretion of Galantamine in Rats, Dogs, and Humans", Drug Metabolism and Disposition, (2002) vol. 30, No. 5, pp. 553-563.

Adrian C. Williams, et al., "Penetration enhancers", Advanced Drug Delivery Reviews, 64 (2012), pp. 128-137.

Murray A. Raskind, et al., "Update on Alzheimer Drug (Galantamine)", The Neurologists, Sep. 2003, vol. 9, No. 5, pp. 235-240.

J Corey-Bloom, Galantamine: a review of its use in Alzheimer's disease and vascular dementia, Int. J. Clin. Pract. Apr. 2003, vol. 57, No. 3, pp. 219-223.

Rhea Brent, et al., Investigating Differences in Solubility Between Crystalline and Amorphous Forms of Pharmaceuticals, Pharmaceutical Analytical Research and Development, May 14, 2005.

N.S. Chandrashekar, et al., Physicochemical and Pharmacokinetic Parameters in Drug Selection and Loading for Transdermal Drug Delivery, Indian Journal of Pharmaceutical Sciences, vol. 70, No. 1, Jan.-Feb. 2008, pp. 1-95.

Amjad Alhalaweh, et al., Physical stability of drugs after storage above and below the glass transition temperature: Relationship to glass-forming ability, International Journal of Pharmaceutics, 495 (Sep. 1, 2015), pp. 312-317.

Patole Bhushan Shankar, et al., Patches: A Novel approach for development of topical drug delivery system, Journal of Advanced Pharmacy Education & Research, Oct.-Dec. 2013, vol. 3, Issue 4, pp. 347-358.

TRANSDERMAL DELIVERY SYSTEM CONTAINING GALANTAMINE OR SALTS THEREOF

CROSS-REFERENCE TO RELATED PATENT APPLICATIONS

This application is a continuation of U.S. patent application Ser. No. 13/985,994, filed Aug. 16, 2013 and claims priority of KR 10-2011-0014530, filed Feb. 18, 2011, all of which are incorporated by reference in their entireties.

TECHNICAL FIELD

The present invention relates to a transdermal delivery system comprising galantamine or its salt as an active ingredient, more specifically to a transdermal delivery system comprising a drug-containing matrix layer, the matrix of which is formed with a styrene-butadiene-styrene copolymer or a styrene-isoprene-styrene copolymer as an adhesive.

BACKGROUND ART

Alzheimer's disease is the most common form of dementia. It is a neurological disease characterized by loss of mental ability, severe enough to interfere with normal activities of daily living. Alzheimer's disease usually occurs in old age, and is marked by a decline in cognitive functions such as remembering, reasoning, and planning. The median survival time for affected patients is approximately 8 years from the onset of symptoms (Coyle, J., Kershaw, P., 2001. Galantamine, a cholinesterase inhibitor that allosterically modulates nicotinic receptors: effects on the course of Alzheimers disease. *Biol. Psychiatry.* 49, 289-299). Galantamine is a tertiary alkaloid and a reversible, competitive acetyl cholinesterase inhibitor (Zarotsky, V., Sramek, J. J., Cutler, N. R., 2001. Galantamine hydrobromide: an agent for Alzheimer's disease. *Am. J. Health-Syst. Pharm.* 60, 446-452). Galantamine is effective and well tolerated for symptomatic treatment of Alzheimer's disease; and improves cognition, global function and daily life activities of the patients (Scott, L. J., Goa, K. L., 2000. Galantamine: a review of its use in Alzheimer's disease. *Drugs.* 60, 1095-1122; Corey-Bloom, J., 2003. Galantamine: a review of its use in Alzheimer's disease and vascular dementia. *Int. J. Clin. Pract.* 57, 219-223).

At present, galantamine is available in the market as tablet or oral solution. Oral administration of galantamine is followed by side effects like abdominal pain, nausea, and diarrhea. Therefore, an alternative way of galantamine administration could be helpful for the success of therapy.

Transdermal drug delivery system (TDDS) is advantageous to minimize the gastrointestinal side effects such as nausea and vomiting, which are the most common adverse events leading even to discontinuation of treatment. TDDS offers benefits such as producing sustained and controlled plasma drug concentration, enhancing bioavailability and bypassing first-pass metabolism. Despite these advantages of TDDS, its use is often limited due to the outermost layer of the skin, stratum corneum. Although this layer is only 20-25 μm thick, it provides a potential barrier to the penetration of many compounds and poses a major problem for therapeutic TDDS (Thomas, B. J., Finnin, F. C., 2004. The transdermal revolution. Drug Discov. Today. 9, 697-703. Walters, K. A., Walker, M., Olejnik, O., 1987. Non-ionic surfactant effects on hairless mouse skin permeability characteristics. *J. Pharm. Pharmacol.* 40, 525-529).

Various approaches could be utilized to overcome the impermeability of skin. Among these approaches, chemical enhancers are commonly employed in the TDDS to facilitate the penetration of the administered drug (Williams, A. C., Barry, B. W., 2004. Permeation enhancers. *Adv. Drug Deliver. Rev.* 56, 603-618). It is well known that the enhancing properties of chemical enhancers depend on the physicochemical properties of drugs and other formulation components. In the matrix based TDDS, especially drug in adhesive (DIA) type, pressure sensitive adhesive (PSA, hereinafter referred to as "adhesive") fulfills both the function of adhesion to skin, and serves as formulation foundation. Compatibility among drug, adhesive and enhancer as well as the adhesive property must be considered before the selection of appropriate adhesive.

U.S. Pat. No. 5,700,480 has disclosed a transdermal delivery system, which comprises a reservoir layer containing galantamine, a plasticizer, and a polyacrylate (for example, acrylate copolymer/methacylate copolymer) as an adhesive. The transdermal delivery system according to U.S. Pat. No. 5,700,480 shows very low penetration, i.e., about 2.7 μg/cm$^2$/hr. In order to address such a problem and make drug-loading higher, US Patent Publication No. 2007/0104771A1 has disclosed a transdermal delivery system, which comprises a drug reservoir containing an acrylate polymer having polar funtional monomer component, more than 10% by weight of galantamine, and a permeation enhancer for delivering the galantamine at a flux of greater than 4.5 μg/cm$^2$/hr. However, the transdermal delivery system according to US Patent Publication No. 2007/0104771A1 has the disadvantage that the flux thereof is still low, i.e., 11.35 μg/cm$^2$/hr in maximum (Table 2).

DISCLOSURE

Technical Problem

The present invention provides a transdermal drug delivery system comprising galantamine or its salt as an active ingredient, which can inhibit crystallization of galantamine or its salt, thereby not only stably maintains a therapeutically effective blood concentration for at least 24 hours; but also provides high skin penetration rate.

That is, the present invention provides a transdermal delivery system containing galantamine or its pharmaceutically acceptable salt, which shows high skin penetration rate continuously for more than 24 hours.

Technical Solution

In accordance with an aspect of the present invention, there is provided a transdermal delivery system, which comprises a drug-containing matrix layer comprising: galantamine or its pharmaceutically acceptable salt as an active ingredient; and a styrene-butadiene-styrene copolymer or a styrene-isoprene-styrene copolymer as an adhesive.

In an embodiment of the present invention, the transdermal delivery system may consist of a backing layer, the drug-containing matrix layer, and a release layer.

In the transdermal delivery system according to the present invention, the galantamine or its pharmaceutically acceptable salt may be present in an amount ranging from 0.5 to 20% by weight, preferably 10 to 20% by weight, based on the total weight of the drug-containing matrix layer. And also, the adhesive may be present in an amount ranging from 70 to 95% by weight, based on the total weight of the drug-containing matrix layer.

The transdermal delivery system according to the present invention may further comprise one or more permeation enhancers selected from the group consisting of propylene glycol laurate, lauryl alcohol, triacetin, isopropyl myristate, cineole, polyoxyethylene lauryl ether, oleoyl macrogol glyceride, and caprylocaproyl macrogol glyceride. Preferably, the permeation enhancer may be polyoxyethylene lauryl ether. The permeation enhancer may be present in an amount ranging from 0.5 to 10% by weight, preferably in an amount of about 5% by weight, based on the total weight of the drug-containing matrix layer.

In the transdermal delivery system according to the present invention, the drug-containing matrix layer may have a thickness ranging from 50 μm to 100 μm, preferably, 50 μm to 80 μm.

Advantageous Effects

The transdermal delivery system according to the present invention comprises a matrix obtained by using a styrene-butadiene-styrene copolymer or a styrene-isoprene-styrene copolymer as an adhesive, which inhibits crystallization of galantamine or its salt in the matrix, thereby being able to stably maintain a therapeutically effective blood concentration for at least 24 hours. Especially, the transdermal delivery system according to the present invention can provide high skin penetration rate, e.g., 38 μg/cm$^2$/hr in maximum.

BEST MODE

Figure 1:
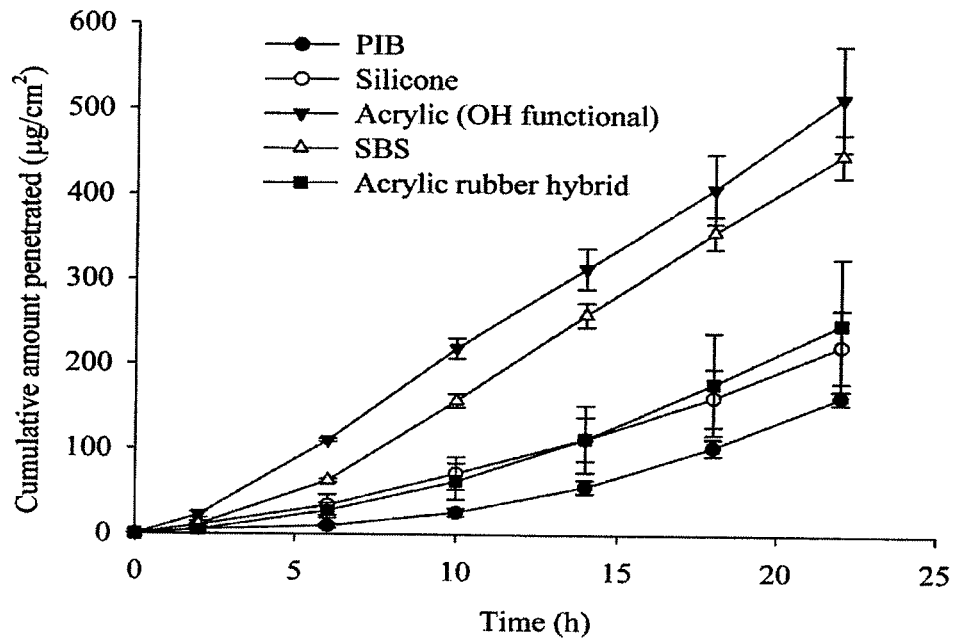
FIG. 1 shows the results obtained by evaluating the effect of types of the adhesive on the permeation of galantamine across the hairless mouse skin at 15% w/w of drug load. Values are expressed as mean±standard deviation. (n=3)

The present invention provides a transdermal delivery system, which comprises a drug-containing matrix layer comprising: galantamine or its pharmaceutically acceptable salt as an active ingredient; and a styrene-butadiene-styrene copolymer or a styrene-isoprene-styrene copolymer as an adhesive.

In order to address the problem of low skin penetration in the conventional transdermal delivery system using acrylic adhesives, the present inventors carried out various researches on characteristics of adhesives, drug concentrations, thicknesses of matrix, permeation enhancers, etc. It is found by the present invention that the low penetration rate is due to the interaction between the tertiary amine group in galantamine and the carboxylic functional group in adhesives; and is due to the crystallization of galantamine in the matrix in which acrylic adhesive is used. And also, the present inventors found that, when a drug-containing matrix layer is designed by using a specific adhesive (i.e., a styrene-butadiene-styrene copolymer or a styrene-isoprene-styrene copolymer), the interaction between galantamine and an adhesive as well as the crystallization of galantamine is effectively inhibited, thereby being able to accomplish high skin penetration.

The adhesive, i.e., a styrene-butadiene-styrene copolymer or a styrene-isoprene-styrene copolymer, not only performs adhesive function but also forms a drug foundation or base. The adhesive may be present in an amount ranging from 70 to 95% by weight, preferably ranging from 80 to 90% by weight, but not limited thereto.

In the transdermal delivery system according to the present invention, the galantamine or its pharmaceutically acceptable salt (for example, HBr salt) may be used in an amount sufficient to obtain a therapeutically effective blood concentration, for example, in an amount ranging from 0.5 to 20% by weight, preferably from 10 to 20% by weight, more preferably from 10 to 15% by weight, especially preferably about 15% by weight, based on the total weight of the drug-containing matrix layer. If the amount of galantamine or its pharmaceutically acceptable salt is less than 0.5% by weight, the size (i.e., area) of the transdermal delivery system for obtaining desired therapeutic is effects of the drug may become excessively large, thereby lowering patients' drug compliance. In addition, if the amount of galantamine or its pharmaceutically acceptable salt is more than 20% by weight, drug crystals may be formed in the drug-containing matrix layer, which results in reducing adhesive force or lowering penetration rate of the drug.

And also, the transdermal delivery system according to the present invention may comprise a permeation enhancer. The permeation enhancer may be present in an amount ranging from 0.5 to 10% by weight, preferably about 5% by weight, based on the total weight of the drug-containing matrix layer, although the amount thereof varies depending on the kinds of permeation enhancer. If the amount of a permeation enhancer is less than 0.5% by weight, it may be difficult to obtain sufficient penetration enhancing effect. In addition, if the amount of a permeation enhancer is more than 10% by weight, the penetration enhancing effect is not increased significantly. The use of a permeation enhancer in excessive amount may result in reducing an adhesive force to the skin; or bring about cold flow due to weaken cohesive force.

The permeation enhancer may be one or more selected from the group consisting of propyleneglycol laurate [for example, Lauroglycol® FCC], lauryl alcohol, triacetin, isopropyl myristate, cineole, polyoxyethylene lauryl ether [for example, Brij™ 30, Brij™ 52, etc.), oleoyl macrogol glyceride (or polyethylene glycol-8 glyceryl linoleate) [for example, Labrafil® 2609, etc.], and caprylocaproyl macrogol glycerides (or polyethylene glycol-8 glyceryl caprylate/caprate) [for example, Labrasol®, etc.]. Among them, polyoxyethylene lauryl ether may be preferably used.

In the transdermal delivery system according to the present invention, the drug-containing matrix layer may have a thickness ranging from 50 μm to 100 μm, preferably, 50 μm to 80 μm.

In an embodiment of the present invention, there is provided a transdermal delivery system comprising a drug-containing matrix layer having a thickness of about 80 μm, the drug-containing matrix consisting of about 15% by weight of galantamine, about 5% by weight of polyoxyethylene lauryl ether, and the remaining amount of a styrene-butadiene-styrene copolymer.

The transdermal delivery system of the present invention may consist of a backing layer, the drug-containing matrix layer, and a release layer. The transdermal delivery system of the present invention consisting of a backing layer, the drug-containing matrix layer, and a release layer may be prepared by forming the drug-containing matrix layer on a release layer and then forming a backing layer thereon. For the release layer, conventional release liners or their laminates used in the field of a transdermal delivery system may be used. For example, there may be used a film, a paper, or a laminates thereof, which is made of polyethylene, polyester, polyvinyl chloride, polyvinylidene chloride, etc. coated with silicone resin or fluoride resin. And also, drug non-absorbable and flexible materials conventionally used in the field of a transdermal drug delivery system may be used as the backing layer (also referred to as "backing membrane"). For example, there may be used polyolefin, polyether, a multi-layer ethylene vinyl acetate film, polyester, polyurethane, etc. The transdermal delivery system of the present invention may be prepared, for example by dissolving galantamine or its pharmaceutically acceptable salt in an appropriate solvent (e.g., chloroform, etc.); mixing a styrene-butadiene-styrene copolymer or a styrene-isoprene-styrene copolymer (and if necessary, a permeation enhancer) therewith; casting the resulting mixture on a release liner coated with e.g., silicone, followed by drying the mixture; and then laminating a backing layer thereon.

The present invention will be described in further detail with reference to the following examples. These examples are for illustrative purposes only and are not intended to limit the scope of the present invention.

1. Materials and Methods (1) Materials

Lauroglycol® FCC, lauryl alcohol, triacetin, isopropyl myristate, cineole, polyoxyethylene lauryl ether (e.g., Brij™ 30, Brij™ 52, etc.), oleoyl macrogol glyceride (e.g., Labrafil® 2609 CS, etc.], and caprylocaproyl macrogol glyceride (e.g., Labrasol®, etc.)

Galantamine was purchased from Ivax Pharmaceuticals (Opava-Komarot, Czech Republic). Polyethylene glycol-8 glyceryl caprylate/caprate (Labrasol®) was obtained from Gattefosse (Gennevillers, France). Polyethylene glycol-8 glyceryl linoleate (Labrafil® 2609) was purchased from Masung Co. (Seoul, Korea). Oleic acid, propylene glycol and sorbitan monooleate (Span® 80) were purchased from Junsei Chemical (Tokyo, Japan). Isopropyl myristate (IPM) and PEG-20 almond glyceride (Crovol® A40) were obtained from Croda (Parsippany, N.J., USA). Cineole, Lauryl alcohol and Brij® 30 were purchased from Sigma Chemical (St. Louis, Mo., USA). Acrylic, polyisobutylene (PIB) and styrene-butadiene-styrene copolymer (SBS) adhesive solutions, in organic solvents, were obtained from National Starch and Chemical Company (Bridgewater, N.J., USA). Silicone adhesive solution (BioPSA® 7-4302) was obtained from Dow Corning (Midland, Mich., USA). All other chemicals were of reagent grade or above and were used without further purification.

(2) Methods

<1> Preparation of Adhesive Matrix Containing Galantamine

Drug solution was prepared by dissolving galantamine in chloroform and mixed with enhancer and adhesive. The resulting mixture was casted onto the release liner. It was set at room temperature for 10 minutes, and subsequently dried at 80° C. for 20 minutes to remove the residual organic solvents. After removal of the solvents, dried film was laminated with a polyester backing film (ScotchPak® 9728, 3M, USA).

<2> Skin Membrane Preparation

Full thickness skin was excised from hairless mice aged 6-8 weeks. The mice were sacrificed humanely under anesthetic condition with diethyl ether. Subcutaneous fat, tissue and blood vessel were carefully removed with scissors and scalpel. Only the skin free of holes or any other defects was used. To perform the in vitro skin permeation study, the skin was cut into pieces of around 6 $cm^2$.

<3> In Vitro Transdermal Permeation Experiment

The in vitro transdermal permeation behavior of galantamine from transdermal delivery system across hairless mouse skin was investigated by using modified Franz diffusion cells. Flow-through diffusion cell system was used and the temperature was maintained at 37 □. The surface area of receiver cell opening was 2 $cm^2$, and its volume 5.5 mL. The receiver cell was filled with phosphate buffer solution (pH 6.0), and the media was stirred by teflon-coated magnetic bar at 500 rpm. The excised skin was mounted onto each receiver cell. O-ring and cell cap were placed on the top of each skin. These components were then clamped. The samples were collected every 4 hours for 24 hours and assayed by high performance liquid chromatography (HPLC).

<4> Analytical Method

Galantamine was analyzed using previously reported method (Ang, C., Fen, H. E., Sub, H. E., 2006. Pharmacokinetics of galantamine Hbr in plasma and brain of mice. *Chin. J. Pharm.* 37, 55-61) with slight modification. HPLC system (Shimadzu Scientific Instruments, MD) consisting of a UV detector (SPD-10A), C18 column (4.6×100 mm, 5 μm, Gemini), a pump (LC-10AD), and an automatic injector (SIL-10A) was used. The wavelength of the UV detector was 230 nm; the column temperature was maintained at 30 □; the flow rate was 1 mL/min; and injection volume was 30 μL. The mobile phase consisted of methanol/water with 0.2% triethylamine adjusted to pH 6.4 by phosphoric acid (35/65, v/v).

<5> Data Deduction

The permeation data were analyzed by the method developed for flow through diffusion cell system (Choi, H-K., Angello, J., 1994. The Mathematical analysis and optimization of a flow through diffusion cell system. *Pharm. Res.* 11, 595-599).

2. Results and Discussion (1) Effect of Adhesive

Selection of appropriate adhesive matrix is important in designing TDDS. It is well known that the physicochemical properties of adhesive can significantly affect the flux of drug across the skin (Subedi, R. K., Jang, J. H., Kim, Jae-II, Park, Y. J., Choi, H.-K., 2010. Formulation and evaluation of transdermal patch containing sibutramine. *J. Kor. Pharm. Sci.* 40, 33-38). The effect of adhesive matrix on the permeation of galantamine was investigated using acrylic, acrylic rubber hybrid, SBS, silicone and PIB matrices. The physicochemical properties of adhesives screened are given in the Table I.

TABLE 1

Physicochemical properties of the adhesives used in the study

| Trade name | Chemical Composition | Functional group |
|---|---|---|
| Durotak ® 87-2510 | Acrylate | OH |
| Durotak ® 87-504 A | Acrylate rubber hybrid | OH |
| Durotak ® 87-2979 | Acrylate vinyl acetate | OH/COOH |
| Durotak ® 87-9301 | Acrylate copolymer | Non functional |
| SBS 6174 | Thermoplastic rubber block copolymer | Non functional |
| BIO-PSA ® 7-4302 | Siloxane | Non functional |
| PIB 10711-62 | Polyisobutylene | Non functional |

Figure 2:
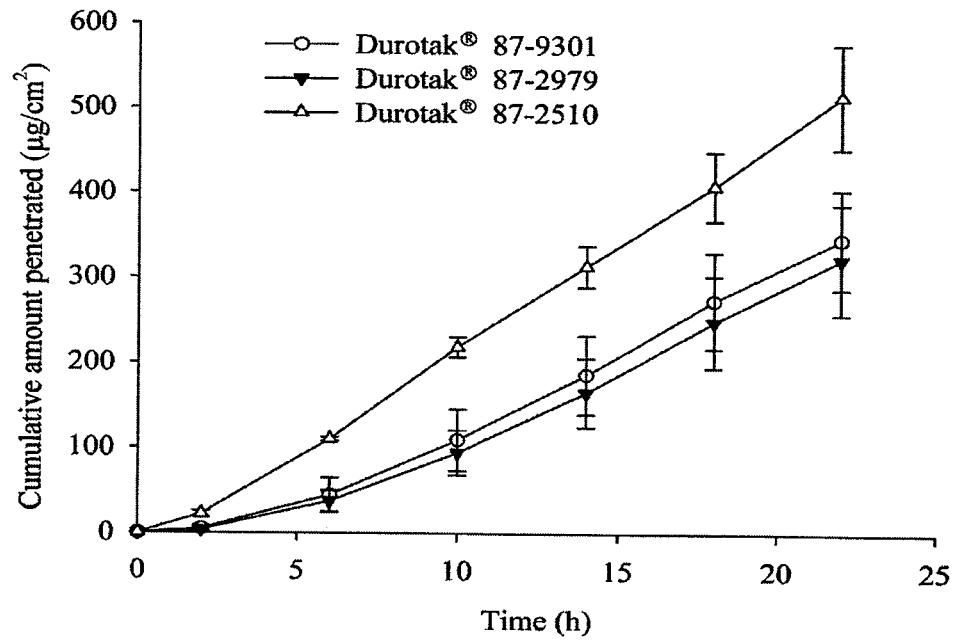
FIG. 2 shows the results obtained by evaluating the effect of functional group in acrylic adhesive on the permeation of galantamine at 15% w/w of drug load. Values are expressed as mean±standard deviation. (n=3)

The patches containing acrylic, acrylic rubber hybrid, SBS, silicone and PIB matrices were screened at 15% w/w drug load. The permeation rate of galantamine was highest from acrylic adhesive followed by SBS, acrylic rubber hybrid, silicone and PIB (see FIG. 1). The effect of different functional groups in acrylic adhesive on the permeation of galantamine was also studied (see FIG. 2). The highest permeation of galantamine was observed from the matrix containing acrylic adhesive with a hydroxyl functional group (Duro-Tak® 87-2510). The lowest permeation of galantamine was observed from acrylic adhesive containing carboxyl functional group (Duro-Tak® 87-2979). This could be due to the interaction of the tertiary amine group in galantamine with the —COOH group in Duro-Tak® 87-2979. The possibility of this type of drug polymer interaction is widely reported (Kim, J. H., Cho Y.-J., Choi, H.-K., 2000. Effect of vehicles and pressure sensitive adhesives on the permeation of tacrine across hairless mouse skin. *Int. J. Pharm.* 196, 105-113; Morimoto, Y., Kokubo, T., Sugibayashi, K., 1992. Diffusion of drug in acrylic type pressure sensitive adhesive matrix. II. Influence of interaction. *J. Control. Release.* 18, 113-121; Subedi, R. K., Jang, J. H., Kim, Jae-II, Park, Y. J., Choi, H.-K., 2010. Formulation and evaluation of transdermal patch containing sibutramine. *J. Kor. Pharm. Sci.* 40, 33-38).

Figure 3:
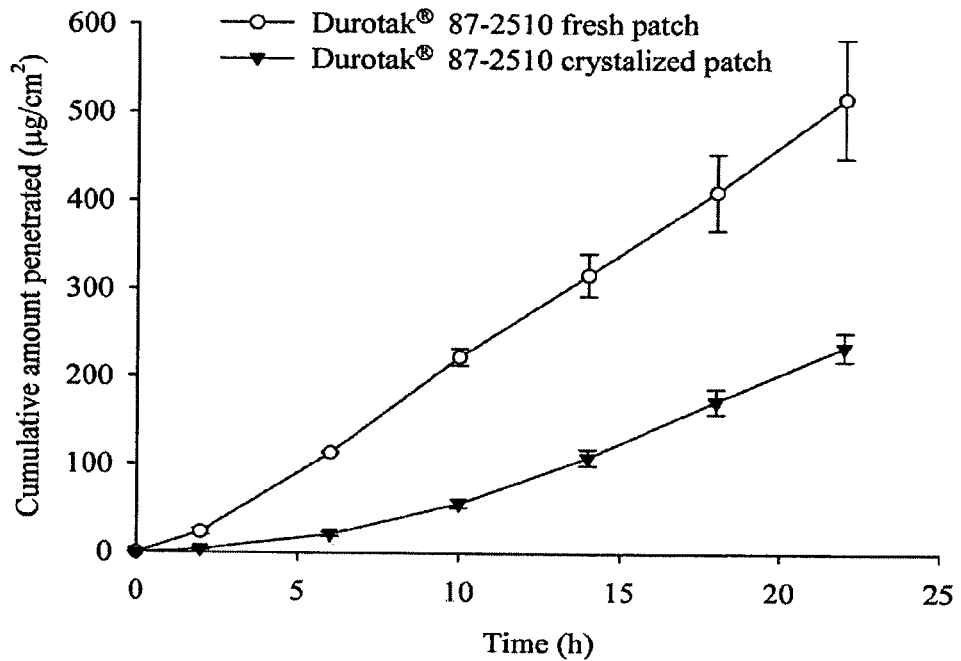
FIG. 3 shows the results obtained through the comparison between fresh and crystallized patch prepared using acrylic adhesive with hydroxyl functional group (Duro-Tak® 87-2510) at 15% w/w of drug load. Values are expressed as mean±standard deviation. (n=3)

Surprisingly, when the patches were stored at room temperature, it is observed that crystals were developed in all the matrices, except SBS, within a week. Although highest flux was obtained from fresh samples prepared in acrylic matrix with hydroxyl functional group, the crystallization of the drug in the patch caused significant reduction in flux of the drug (see FIG. 3). Considering drug loading capacity, appropriate permeation rate, and good adhesive properties, it is determined that the SBS matrix is most excellent.

(2) Effect of Galantamine Concentration on Skin Permeation

Figure 4:
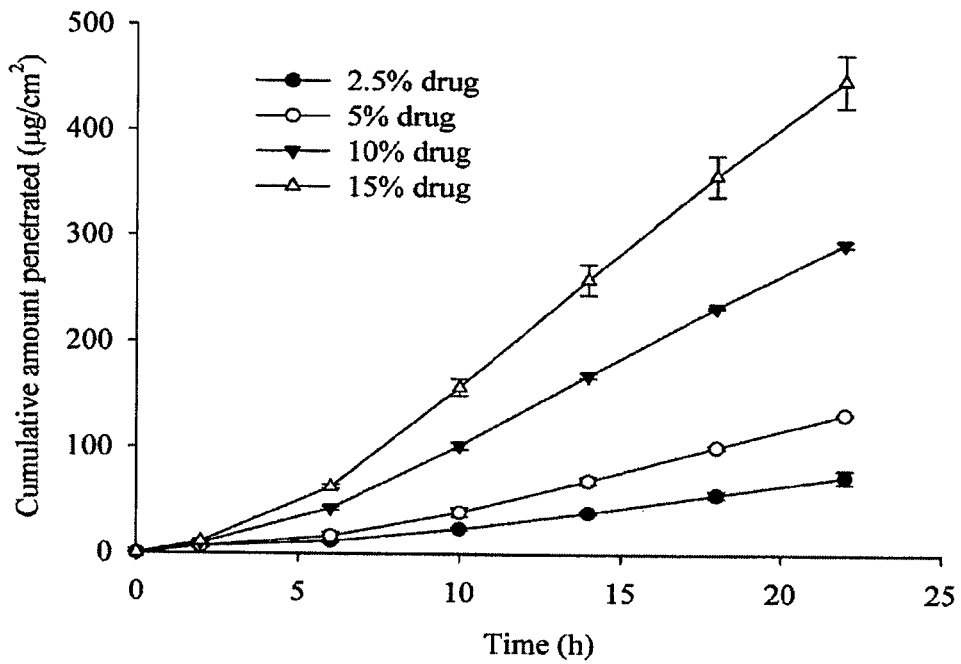
FIG. 4 shows the results obtained by evaluating the effect of drug loading in SBS matrix on the permeation of galantamine across hairless mouse skin at dried matrix thickness of 80 μm. Values are expressed as mean±standard deviation. (n=3)
Figure 5:
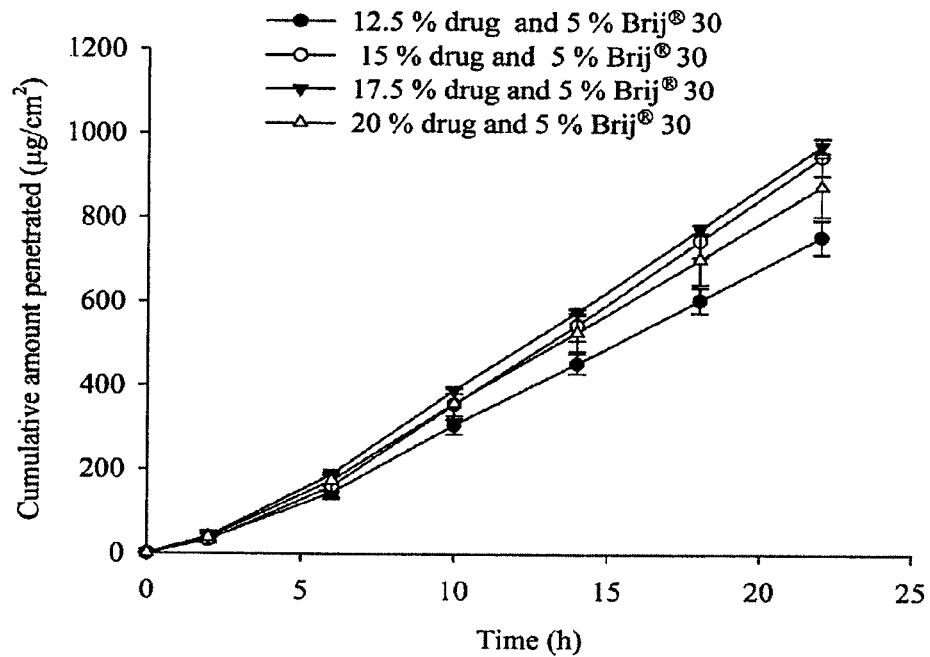
FIG. 5 shows the results obtained by evaluating the effect of drug loading in the presence of enhancer on the permeation of galantamine in SBS matrix. Values are expressed as mean±standard deviation. (n=3)

FIG. 4 shows the effect of drug loading in SBS matrix on the permeation of galantamine across the hairless mouse skin. When drug loading was increased from 2.5 to 15% w/w of polymer weight, permeation rate also increased proportionally. The correlation coefficient obtained between galantamine concentration in the patch and the average cumulative flux was $R^2=0.998$. At drug loading of 20% w/w, crystals were observed in the matrix within 72 hours. Galantamine might have been supersaturated in the SBS matrix at concentrations above 15% w/w, which led to recrystallization of the drug in the matrix. Further increase in the drug load did not lead to significant increase in permeation. To optimize drug loading, the effect of drug loading on the flux of galantamine was also studied in the presence of an enhancer. FIG. 5 shows the effect of drug loading from 12.5% w/w to 20% w/w, in the presence of 5% v/w Brij® 30. The permeation of galantamine increased significantly up to 15% w/w of drug load. However, beyond 15% w/w of drug load, flux remained almost constant, and it even decreased at 20% w/w of drug load. This decrease in flux could be due to the crystallization of galantamine in the matrix. Therefore, it is determined that the most excellent drug loading is at 15% w/w.

(3) Effect of Matrix Thickness

Figure 6:
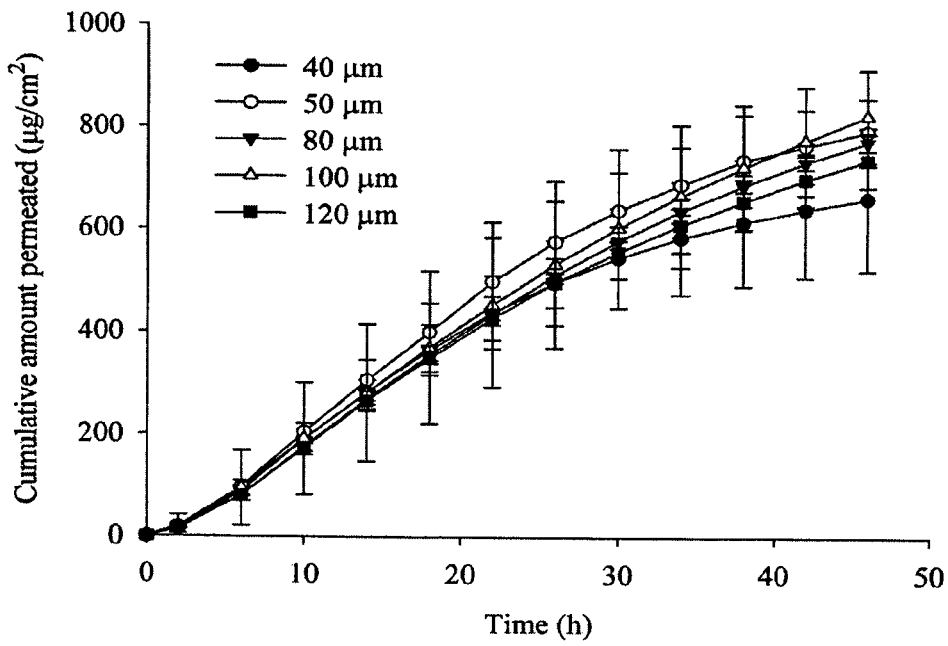
FIG. 6 shows the results obtained by evaluating the effect of dried thickness of SBS matrix on the permeation of galantamine at 15% drug load for 48 hours. Values are expressed as mean±standard deviation. (n=3)

The thickness of the matrix layer is one of the important parameters in the development of matrix-based TDDS. Thicker matrix is able to deliver higher amount of drug to the skin over relatively longer application time (Furuishi, T., Io, T., Fukami, T., Suzuki, T., Tomono, K., 2008. Formulation and in vitro evaluation of pentazocine transdermal delivery system. *Biol. Pharm. Bull.* 31, 1439-1443). It is due to higher amount of drug available for permeation from the patch. However, thicker matrix also has higher tendency to cause cold flow (Wokovich, A. M., Prodduturi, S., Doub, W. H., Hussain, A. S., Buhse, L. F., 2006. Transdermal delivery system (TDDS) adhesion as a critical safety, efficacy and quality attribute. *Eur. J. Pharm. Biopharm.* 64, 1-8). Therefore, effect of thickness was studied in the galantamine loaded patches to evaluate the permeation as well as adhesion characteristics. During 24 hour study, it was not possible to distinguish the permeation characteristics from matrices with various thicknesses. Prolonging the study up to 48 hours, thicker adhesive matrices showed better and consistent profile (see FIG. 6). Especially, thinner matrix (40 μm) showed a declining permeation profile. The adhesive properties of the prepared patches were manually evaluated by thumb tack test. As a result thereof, it was found that matrix thickness above 50 μm possessed sufficient adhesive force. Beyond matrix thickness of 80 μm, flux did not increase significantly and the profile obtained was almost similar. As mentioned in the above, thicker matrix may not be desirable since it could result in cold flow upon applying on the skin. Therefore, considering the adhesiveness and potential cold flow, it is determined that the matrix thickness is preferably 50 μm to 80 μm, most preferably 80 μm.

(4) Effect of Permeation Enhancer

Permeation enhancer reversibly reduces the permeability barrier of the stratum corneum. Permeation enhancers can also act as a plasticizer, increasing the mobility of the drug in the matrix. We evaluated the effects of various permeation enhancers (5% v/w) in SBS matrix with 15% w/w drug load. The results thereof are shown in Table 2.

TABLE 2

| Permeation enhancer | Enhancement ratio* |
|---|---|
| Control | 1.00 ± 0.00 |
| Lauryl alcohol | 1.28 ± 0.10 |
| Labrafil ® 2609 | 1.28 ± 0.03 |
| Labrasol ® | 1.16 ± 0.07 |
| Propylene glycol | 0.76 ± 0.06 |
| Span ® 80 | 1.09 ± 0.07 |
| Crovol ® A40 | 0.98 ± 0.02 |
| Isopropyl myristate (IPM) | 1.26 ± 0.14 |
| PEG 400 | 0.92 ± 0.01 |
| Brij ® 30 | 1.68 ± 0.08 |
| Cineole | 1.12 ± 0.03 |
| Triacetin | 1.19 ± 0.01 |
| Glycerin | 0.86 ± 0.01 |

TABLE 2-continued

| Permeation enhancer | Enhancement ratio* |
|---|---|
| Lauroglycol® FCC | 1.59 ± 0.04 |
| Transcutol® | 0.80 ± 0.02 |

*Enhancement ratio = Flux with permeation enhancer/Flux without permeation enhancer Among the permeation enhancers screened, Crovol® A40, propylene glycol, polyethylene glycol (PEG) 400, Transcutol® and glycerin did not enhance the permeation of galantamine. Whereas Lauroglycol® FCC, lauryl alcohol, triacetin, Isopropyl myristate (IPM), cineole, Brij® 30, Labrafil® 2609 and Labrasol® significantly enhanced the permeation of galantamine. Among them, Brij® 30 and Lauroglycol® FCC showed comparatively higher enhancement ratio for galantamine. The enhancing effect of Brij® 30, which showed the highest enhancement ratio, on the skin permeation of galantamine was evaluated at different concentrations (2.5 to 10% v/w of polymer weight), with 15% w/w of drug load. An increasing trend in the permeation of galantamine was observed with an increase in the permeation enhancer concentration (see FIG. 7). Significant increase in permeation profile was observed when the level of Brij® 30 increased from 2.5 to 5% v/w. However, the increase in permeation was not much pronounced beyond 5% v/w of Brij® 30 concentration. Furthermore, in the patches containing more than 5% v/w of Brij® 30, significant decrease in adhesiveness was observed. Hence, considering the permeation and adhesive properties, it is determined that the optimum level of Brij® 30 in the patch is about 5% v/w.

3. Conclusions

From the above study, the flux of 38 µg/cm$^2$/h can be obtained from the optimized formulation. e.g., the transdermal delivery system comprising a drug-containing matrix layer having a thickness of about 80 µm, the drug-containing matrix consisting of about 15% by weight of galantamine, about 5% by weight of polyoxyethylene lauryl ether, and the remaining amount of a styrene-butadiene-styrene copolymer. Therefore, it is considered that even the patch size smaller than 9 cm$^2$ can deliver 8 mg of galantamine per day.

The invention claimed is:

1. A galantamine transdermal delivery system comprising a backing layer, a drug-containing matrix layer, and a release layer, wherein the drug-containing matrix layer consists of: (i) galantamine or its pharmaceutically acceptable salt as an active ingredient that is free of crystallized galantamine, (ii) a styrene-butadiene-styrene copolymer, and (iii) propylene glycol laurate, wherein galantamine or its pharmaceutically acceptable salt is 0.5 to 20% by weight, wherein the styrene-butadiene-styrene copolymer is 70-95% by weight, based on total weight of the drug-containing matrix layer, and wherein propylene glycol laurate is 0.5-10% by weight, based on the total weight of the drug-containing matrix layer.

2. The galantamine transdermal delivery system of claim 1, wherein propylene glycol laurate is 5% by weight, based on the total weight of the drug-containing matrix layer.

3. The galantamine transdermal delivery system of claim 1, wherein the drug-containing matrix layer has a thickness from 50 µm to 80 µm.

4. The galantamine transdermal delivery system of claim 1, wherein the styrene-butadiene-styrene copolymer is 80-90% by weight, based on total weight of the drug-containing matrix layer.

5. The galantamine transdermal delivery system of claim 1 wherein the propylene glycol laurate is lauroglycol.

6. The galantamine transdermal delivery system of claim 1, wherein the galantamine or its pharmaceutically acceptable salt is effective for up to 24 hours.

7. The galantamine transdermal delivery system of claim 1, wherein the galantamine or its pharmaceutically acceptable salt has a flux rate of up to 38 µg/cm2/hr.

* * * * *